United States Patent [19]

Klee et al.

[11] 3,940,994

[45] Mar. 2, 1976

[54] HIGH PRESSURE SAMPLE INJECTION APPARATUS AND METHOD

[75] Inventors: Richard E. Klee, Napa; Joseph A. Varozza, III, Saratoga, both of Calif.

[73] Assignee: Varian Associates, Palo Alto, Calif.

[22] Filed: Aug. 1, 1974

[21] Appl. No.: 493,593

[52] U.S. Cl............................................ 73/422 GC
[51] Int. Cl.[2]..................................... G01N 1/10
[58] Field of Search......................... 73/422, 61.1 C

[56] References Cited
UNITED STATES PATENTS

| | | | |
|---|---|---|---|
| 3,184,973 | 5/1965 | Bradley............................ | 73/422 R |
| 3,186,234 | 6/1965 | Solnick........................... | 73/422 GC |
| 3,501,176 | 3/1970 | Arms.............................. | 73/422 GC |

OTHER PUBLICATIONS

Abel, Kenneth, Gas Sampling Valve for Closed System Sampling, Analytical Chemistry, Vol. 38, No. 6, May, 1966, pp. 806–807.

*Primary Examiner*—S. Clement Swisher
*Attorney, Agent, or Firm*—Stanley Z. Cole; John J. Morrissey

[57] ABSTRACT

A high pressure sample injector for liquid chromatographs is disclosed. The apparatus includes structure defining a cylindrical dispensing chamber for receiving the sample to be injected into the flow path of a high pressure stream of carrier fluid in a liquid chromatograph. Control structure is interposed between the dispensing chamber and the flow path of the carrier stream for preventing liquid flow from the carrier stream to the dispensing chamber, and for enabling flow in the opposite direction only when the pressure in the dispensing chamber at least equals the carrier stream pressure. A pressurizing apparatus is connected to the dispensing chamber to raise its pressure, when desired, to a value at least equal to that of the carrier stream, in order that the sample may be injected into the carrier without reducing the carrier stream pressure.

13 Claims, 4 Drawing Figures

HIGH PRESSURE SAMPLE INJECTION APPARATUS AND METHOD

BACKGROUND OF THE INVENTION

1. Field of the Invention.

This invention relates to method and apparatus for injecting samples of material into a high pressure environment. More particularly, the invention pertains to sample injection apparatus for use in liquid chromatography.

2. Description of the Prior Art.

Liquid chromatography pertains to a particular variety of equipment and techniques for analyzing the components of an unknown sample of liquid material, qualitatively and/or quantitatively. According to chromatographic techniques, a column is provided which is packed with a finely divided material. The packing material provided is chosen in accordance with its affinity for attracting certain elements to adsorb or cling to it. The sample is forced in a stream of carrier liquid through the column, and each of the components passes through the column in a time pattern which is a function of the degree of tendency of that particular component to be adsorbed by the packing material. By detecting variations in properties of the liquid emerging from the column, and plotting these variations against time, certain information can be derived as to the nature and amount of the components of the unknown sample. For example, the presence of a given component of the sample may be known to effect a change in a particular property of the liquid emerging from the column such that a maximum value of that property will occur at a predetermined time after the sample is introduced into the column. By observing where such peaks occur, the nature of various components of the sample may be determined with a significant degree of certitude and repeatability.

It has been found that if the sample is driven through the column in a carrier stream at very high pressure, a consequent reduction in the time for analysis of each sample is observed, due to the more rapid passage of the sample through the column. Such high pressure techniques have certain disadvantages, however.

There is difficulty and great expense in procuring and manufacturing seals which are sufficient to handle the extreme pressure drops which often occur between the sample injectors and the stream into which the sample is to be forced. Often, these pressure drops result in leakage and consequent inaccuracy of analysis.

In the past some effort has been made to obviate this problem by stopping the flow of carrier liquid in the high pressure line to the column during injection. This is time consuming and requires frequent starting and stopping of the high pressure pumps for driving liquid through the column, which increases wear on such components and their control elements.

Even when high pressure injection has been possible, it often results in a momentary drop in the carrier line pressure which adversely affects resolution of the system.

It is therefore an object of this invention to provide a method and apparatus for introducing a sample of material into a very high pressure line of flowing carrier liquid, without interrupting the flow of liquid in the line or reducing the line pressure.

SUMMARY OF THE INVENTION

The injector of the present invention is preferably employed in connection with a liquid chromatograph having a pump for delivering a carrier liquid along a high pressure line to an analysis column. The effluent from the column is analyzed by a detector for qualitatively and/or quantitatively analyzing the contents of the effluent. The sample to be tested is delivered by the injector of this invention into the high pressure carrier stream line upstream of the column.

The injector includes structure which defines a dispensing chamber for holding the sample, from which chamber the sample is injected over a path into the carrier stream. A control structure is interposed between the dispensing chamber and the carrier stream which substantially prevents any liquid flow from the carrier stream into the dispensing chamber, and which enables liquid flow from the dispensing chamber to the carrier stream only in response to pressure of the dispensing chamber becoming equal to or greater than that of the carrier stream. The injector also includes pressurizing apparatus for controlling the pressure of the dispensing chamber as desired in order to govern injection of the sample.

The control structure preferably includes a one-way check valve interposed between the dispensing chamber and the carrier stream. The check valve has structure defining a valve chamber with a ball seat having an orifice interposed in the path communicating between the dispensing chamber and the carrier stream and a checking element in the valve chamber. The checking element is most typically a spherical ball but could be of any other suitable geometrical configuration depending upon seat design; for example, in certain applications a conically shaped checking element might be preferred. Pressure from the carrier stream forces the ball to seat whenever the dispensing chamber pressure is lower than that of the carrier stream, thereby sealing off the dispensing chamber. When the dispensing chamber pressure reaches that of the carrier stream, the ball separates from the seat so that the liquid in the dispensing chamber may flow outwardly into the carrier stream.

Preferably, the dispensing chamber has the form of a hollow cylinder, and the pressurizing apparatus includes a dispensing piston which is slidably positioned in the dispensing chamber. The pressurizing apparatus further includes an actuating structure connected to move the piston in either direction, such that the pressure in the dispensing chamber may be raised or lowered as desired.

The actuating structure includes an actuating cylinder with an actuating piston therein and pneumatic means for applying force to the actuating piston. The actuating piston is perferably connected to the dispensing piston by mechanical linkage so that motion of the actuating piston will also move the dispensing piston.

Preferably, the actuating piston has a cross-sectional area substantially greater than that of the dispensing piston, so that a relatively low pressure applied to the actuating piston is capable of producing a higher pressure in the dispensing chamber.

The injector of this invention also optimally includes a resiliant structure for biasing the actuating piston to move the dispensing piston so as to reduce the pressure in the dispensing chamber in the absence of pneumatic force being applied to the actuating piston.

The preferred embodiment of the injector of this invention also includes a sample reservoir for holding the sample and which communicates with the dispensing chamber by way of an injection septum. When the dispensing piston is moved to reduce the pressure in the dispensing chamber, a measured quantity of the sample liquid is drawn from the reservoir into the dispensing chamber. By control of the amount of dispensing piston movement, the amount of sample liquid drawn into the dispensing chamber can be quite accurately regulated.

The injector of this invention preferably includes a feature whereby the check valve interposed between the dispensing chamber and the carrier stream is capable of withstanding the carrier stream pressures in excess of 10,000 pounds per square inch gage.

DESCRIPTION OF THE PREFERRED EMBODIMENT

Figure 1:
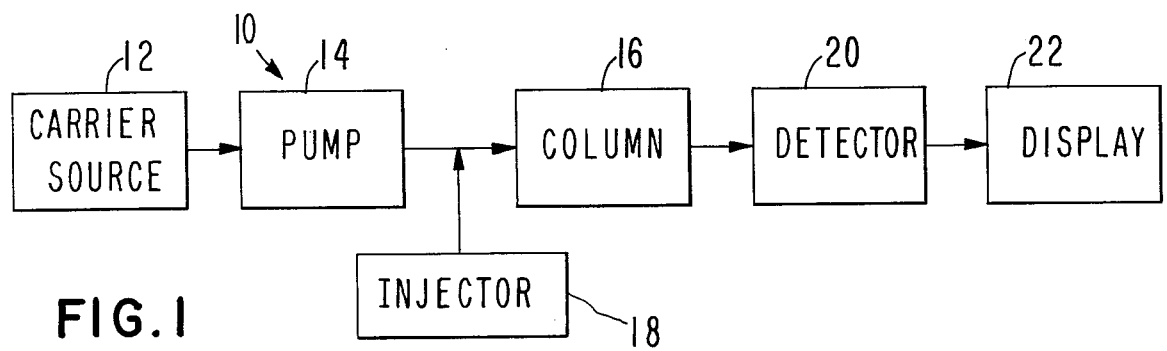
FIG. 1 is a block diagram illustrative of a liquid chromatograph in which the invention of this application is suitably employed.

FIG. 1 illustrates a system 10 comprising a liquid chromatograph in which the injector of this application is employed. The system includes a carrier source or reservoir 12 connected to a pump 14 for delivering a high pressure stream of carrier liquid to an analysis column 16. In actual tests, a pump which delivers a high pressure stream in excess of 10,000 lbs. per square inch gage has been used for the pump 14. The injector 18 adds the sample to be analyzed to the carrier stream intermediate the pump and the column.

A detector 20 monitors variations in one or more properties of the effluent from the column 16 in order to derive information relating to the quantitative and- /or qualitative analysis of the effluent from the column and consequently of the sample input to the carrier stream by the injector 18. Optionally, a display apparatus 22, such as a strip chart recorder, can be connected to the detector for rendering a permanent record of the variations in the detected properties of the effluent.

The injector 18 of this invention injects a predetermined quantity of sample into the high pressure carrier stream without necessitating the stopping of the flow of carrier liquid from the pump to the column, and without producing a drop in pressure in the carrier stream during the injection step.

Figure 2:
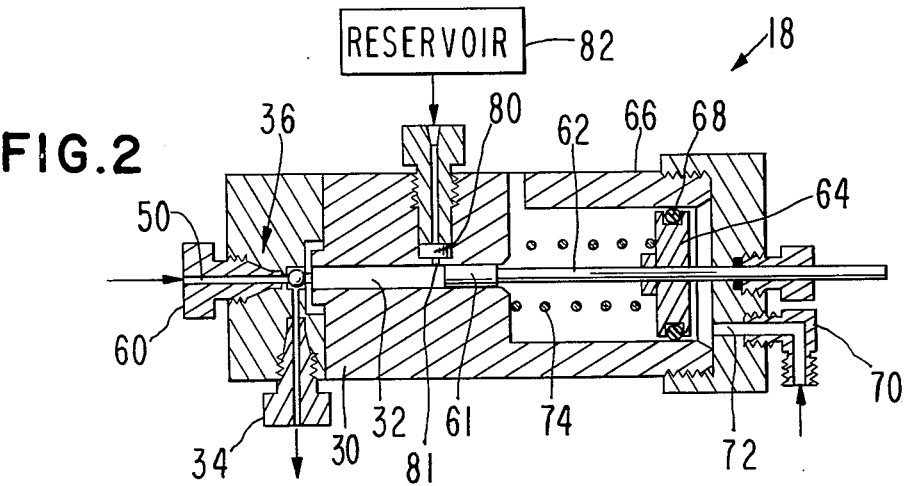
FIG. 2 is an elevational view of the injector of this invention, showing portions thereof in cross-section.

The injector 18 in accordance with this invention is shown in FIG. 2. FIG. 2 shows a structure 30 for defining a cylindrical dispensing chamber 32. The structure 30 may be made of any suitable rigid material, such as stainless steel. Sample material which is to be injected is placed in the dispensing chamber 32 from which it is ejected into the carrier stream by way of a conduit defined by a fitting 34, which communicates with the carrier stream and with the dispensing chamber 32.

A control structure 36 is interposed between the dispensing chamber 32 and the carrier stream. The control structure 36 substantially prevents liquid flow in a direction from the carrier stream to the dispensing chamber 32. The control structure 36 enables liquid flow from the dispensing chamber 32 into the carrier stream only in response to the pressure in the dispensing chamber 32 becoming at least equal to that of the carrier stream.

Figure 3:
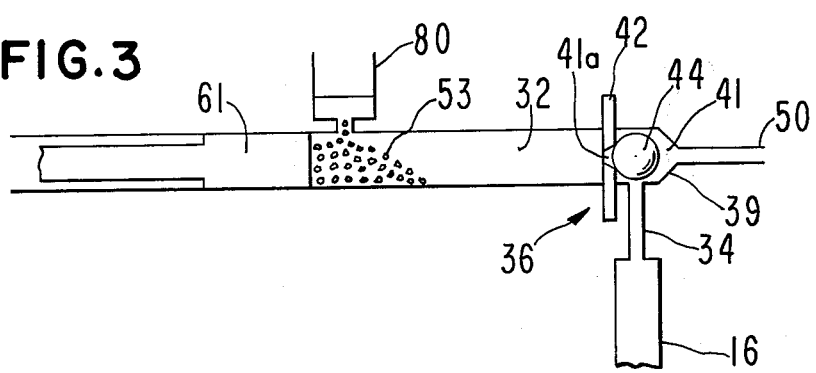
FIG. 3 is a diagrammatic view of a portion of the injector of this invention.
Figure 4:
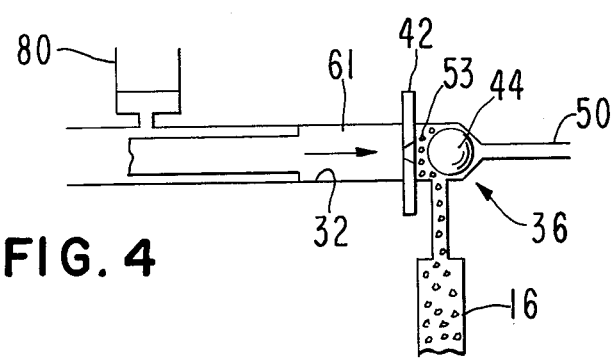
FIG. 4 is another diagrammatic view of a portion of the injector of this invention, illustrating the injector in an operative configuration different from that of FIG. 3.

The control structure 36 is shown in diagrammatic form in FIGS. 3 and 4 as a ball check valve. The check valve 36 includes a structure 39 for defining a valve chamber 41. The carrier stream flows through the valve chamber by way of an inlet port 50 in a fitting 60, and through a fitting 34 having a conduit. The check valve also includes a structure 42 for defining a ball seat which is interposed with an orifice 41a in the path of liquid flow from the dispensing chamber to the valve chamber. Inside the valve chamber is located a ball 44 which is configured to seat firmly in the ball seat 42 when the pressure in the valve chamber exceeds that of the dispensing chamber.

The pressure of the carrier stream is transmitted to the valve chamber. When the carrier stream pressure is greater than that of the dispensing chamber, the ball 44 is forced firmly into the seat 42 and substantially prevents any liquid flow from the valve chamber into the dispensing chamber. The carrier stream flows through the port 50, and thence through the valve chamber 41, into the column 16.

When the pressure in the dispensing chamber becomes at least equal to that of the carrier stream, the ball 44 separates from the seat 42 and permits fluid to flow from the dispensing chamber through the fitting 34 to the column 16; the stream of carrier liquid passes through the port 50 into the valve chamber 41, where it picks up the sample liquid, and moves outwardly toward the column 16. This operation is shown in FIGS. 3 and 4, the sample being indicated by the dots 53. The continuous flow of carrier liquid through the valve chamber purges the valve chamber of sample when the injection step is completed.

Pressurizing apparatus for controlling the pressure in the dispensing chamber is shown in FIG. 2. The pressurizing apparatus includes a dispensing piston 61 which is positioned to slidably move within the dispensing chamber 32. The dispensing piston is connected by a rod 62 to an actuating piston 64. The actuating piston 64 is slidably mounted within an actuating cylinder defined by the structure indicated at 66. An O-ring 68 surrounds the actuating piston 64 in order to provide an effective seal between the actuating piston and the actuating cylinder walls. Movement of the actuating piston 64 induces corresponding movement of the dispensing piston 61 such that the material in the dispensing chamber is compressed and the pressure within that chamber rises.

Power for causing the motion of the actuating piston is provided by an air compressor (not shown) which is connected to deliver controlled high pressure air through a fitting 70 and a conduit 72 communicating with the actuating cylinder.

A spring 74 is interposed within the actuating cylinder to bias the actuating piston in a direction such that the bias movement of the actuating piston will cause the dispensing piston 61 to move to the right as shown in FIG. 2, thus reducing the pressure in the dispensing cylinder. The check valve seals off the dispensing chamber from the carrier stream when this takes place.

Preferably, the cross-sectional area of the actuating piston and cylinder is significantly greater than that of the dispensing piston and cylinder. The reason for this is to enable the generation of very high pressures in the dispensing chamber by application of a relatively lower pressure on the actuating piston, enabling the powering of the actuating piston by a compressed air source and supply system dealing with only moderate pressures.

Structure is provided for causing the ingress of sample material into the dispensing chamber in response to motion of the dispensing piston. As shown best in FIG. 2, a septum 80 extends through the walls of the structure 30 by way of an orifice 81 into the dispensing chamber. When the actuating piston is biased to the right, as indicated in FIG. 2, the dispensing piston also moves to the right to a point which is beyond the septum orifice 81 in the dispensing chamber with respect to the control structure 36. When the dispensing piston moves to the right, the control structure prevents transmission of the pressure from the carrier stream into the dispensing chamber, such that this motion of the dispensing piston reduces the pressure in the dispensing chamber. This reduction of pressure draws in through the septum orifice 81 a quantity of sample material, the amount being dependent on the structure of the steptum and the distance the piston 61 moves to the right of the septum orifice 81.

By adjustment of the relative positions of the actuating and dispensing pistons and/or adjustment of the constraints of motion of the actuating piston, the distance which the dispensing piston moves to the right of the septum orifice can be precisely governed and consequently the amount of sample material drawn into the dispensing chamber by the biased movement of the actuating piston to the right can be similarly governed.

A supply of sample material may be maintained in a sample reservoir 82 which communicates with the dispensing chamber 32 through the septum 81 for multiple injections. Communication from the sample reservoir 82 through the septum orifice 81 into the dispensing chamber 32 may be accomplished by suitable tubing. Alternatively, a pre-measured amount of sample can be placed in the dispensing chamber 32 by manual syringe injection through the septum 80.

It can be seen from the foregoing that the sample injector disclosed herein accomplishes the objects of this invention in that it provides a sample injector for a liquid chromatograph capable of on-stream sample injection into a very high pressure carrier stream without the need for stopping the carrier flow to accomplish the injection and without causing a reduction of pressure in the carrier stream.

The preferred embodiment disclosed here is intended to be illustrative of the invention rather than exhaustive. It is recognized that persons of ordinary skill in the relevant art may be able to make certain modifications, adaptions or new uses of the embodiment disclosed herein without departing from the spirit and scope of this disclosure and the claims.

What is claimed is:

1. An injector for a liquid chromatograph for injecting a sample liquid into a high-pressure stream of carrier liquid, said injector comprising:
    a. structure defining a reservoir for the sample liquid,
    b. structure defining a dispensing chamber for receiving a measured volume of the sample liquid from said reservoir,
    c. structure defining a flow path for the high-pressure stream of carrier liquid,
    d. control structure means interposed between said dispensing chamber and said flow path for substantially preventing liquid flow from said flow path to said dispensing chamber, and for enabling liquid flow from said dispensing chamber to said flow path only when the pressure of said measured volume of sample liquid in said dispensing chamber is at least equal to the pressure of said high pressure stream of carrier liquid, and
    e. displacement means for limiting the volume of sample liquid receivable in said dispensing chamber and for imparting to the sample liquid in said dispensing chamber a pressure at least equal to the pressure of said high-pressure stream of carrier liquid.

2. The injector of claim 1 wherein said control structure means comprises:
    a check valve.

3. The injector of claim 2 wherein said check valve comprises:
    a. structure defining a valve chamber having a ball seat, said ball seat being apertured to enable liquid flow therethrough from said dispensing chamber to said flow path for said high-pressure stream of carrier liquid, and
    b. a ball element disposed in said valve chamber, said ball element being configured to seat firmly in said ball seat when the pressure of the carrier liquid in said valve chamber exceeds the pressure of the sample liquid in said dispensing chamber.

4. The injector of claim 3 wherein:
    said valve chamber is configured so as to be continuously flushed by said high-pressure stream of carrier liquid.

5. The injector of claim 1 wherein:
    a. said dispensing chamber is of cylindrical configuration, and
    b. said displacement means comprises a dispensing piston positioned coaxially within said cylindrical dispensing chamber.

6. The injector of claim 5 wherein:
    said dispensing piston is connected to an actuating piston whereby said dispensing piston is slidably movable within said dispensing chamber in response to force applied to said actuating piston.

7. The injector of claim 6 further comprising:
    resilient means for biasing said actuating piston for moving said dispensing piston within said dispensing chamber so as to reduce the pressure of said sample liquid within said dispensing chamber.

8. The injector of claim 6 wherein:
    said actuating piston has a greater cross-sectional area than does said dispensing piston.

9. The injector of claim 1 wherein:
    said control structure means is constructed to withstand a carrier stream pressure up to and in excess of 10,000 pounds per square inch gage.

10. A method for injecting a sample liquid into a high-pressure stream of carrier liquid in a liquid chromatograph, said method comprising the steps of:
    a. placing a measured volume of said sample liquid in a dispensing chamber,
    b. substantially preventing liquid flow from the stream of carrier liquid to the dispensing chamber, and enabling liquid flow from the dispensing chamber to the stream of carrier liquid only when the pressure of said measured volume of sample liquid in the dispensing chamber is at least equal to the pressure of the stream of carrier liquid, and c. raising the pressure of said measured volume of sample liquid in the dispensing chamber to a value at least equal to the pressure of the stream of carrier liquid.

11. The method of claim 10 wherein said step of placing said measured volume of sample liquid in said dispensing chamber comprises:

a. preliminarily placing a quantity of said sample liquid in a sample reservoir communicable with said dispensing chamber, and b. transferring said measured volume of the sample liquid from said reservoir into said dispensing chamber by displacement means.

12. The method of claim 10 wherein said step of raising the pressure of said measured volume of sample liquid in said dispensing chamber comprises moving a piston within said dispensing chamber after said measured volume of sample liquid has been transferred thereto.

13. The method of claim 11 wherein said step of transferring said measured volume of said sample liquid from said reservoir to said dispensing chamber comprises:

reducing the pressure in said dispensing chamber to draw said sample liquid from said reservoir.

* * * * *